United States Patent
Kooij et al.

(10) Patent No.: US 10,034,995 B2
(45) Date of Patent: Jul. 31, 2018

(54) RETRACTABLE TUBE FOR CPAP

(75) Inventors: Michiel Kooij, Hoogkarspel (NL);
Gerard Michael Rummery, Linden (AU); Robert Edward Henry, Roseville (AU)

(73) Assignee: ResMed Limited, Bella Vista (AU)

( * ) Notice: Subject to any disclaimer, the term of this patent is extended or adjusted under 35 U.S.C. 154(b) by 2834 days.

(21) Appl. No.: 12/211,896

(22) Filed: Sep. 17, 2008

(65) Prior Publication Data
US 2009/0078259 A1    Mar. 26, 2009

Related U.S. Application Data

(60) Provisional application No. 60/973,902, filed on Sep. 20, 2007, provisional application No. 60/987,825, filed on Nov. 14, 2007, provisional application No. 61/031,407, filed on Feb. 26, 2008.

(51) Int. Cl.
*A61M 16/08* (2006.01)
*A62B 9/00* (2006.01)
*F16L 3/13* (2006.01)

(52) U.S. Cl.
CPC ........... *A61M 16/0875* (2013.01); *F16L 3/13* (2013.01); *A61M 2209/088* (2013.01); *A62B 9/00* (2013.01)

(58) Field of Classification Search
USPC ..................................... 128/204.17–205.26
See application file for complete search history.

(56) References Cited

U.S. PATENT DOCUMENTS

| | | | |
|---|---|---|---|
| 2,550,797 A | 5/1951 | Friedman |
| 2,733,734 A | 2/1956 | Woodward et al. |
| 2,739,616 A | 3/1956 | Duff |
| 2,999,497 A | 9/1961 | Hamilton et al. |

(Continued)

FOREIGN PATENT DOCUMENTS

| | | |
|---|---|---|
| CN | 87217508 U | 9/1988 |
| CN | 2152959 Y | 1/1994 |

(Continued)

OTHER PUBLICATIONS

Extended European Search Report dated Dec. 10, 2008 in corresponding EP Application No. 08164639.0 (9 pages).

(Continued)

*Primary Examiner* — Rachel T Sippel
(74) *Attorney, Agent, or Firm* — Nixon & Vanderhye P.C.

(57) ABSTRACT

A retractable tube for use in a respiratory apparatus for delivering a pressurized flow of breathable gas to a patient has an internal diameter of about 30 mm or less, a weight of about 500 g/m or less, and an unextended length of about 2 m or less. The retractable tube includes a portion that is extensible in a range of about 40%-400% in response to force applied to the tube, and the extensible portion is configured to return the tube to its unextended length in the absence of force applied to the tube. A respiratory apparatus for delivering a flow of pressurized breathable gas includes a flow generator to generate the flow and a patient interface to deliver the flow to the patient's airways. The flow generator and the patient interface are connected by a retractable tube. A method of delivering a flow of pressurized breathable gas includes connecting the flow generator and the patient interface using a retractable tube.

71 Claims, 11 Drawing Sheets

(56) References Cited

U.S. PATENT DOCUMENTS

| | | |
|---|---|---|
| 3,080,891 A | 3/1963 | Duff |
| 3,346,187 A | 10/1967 | Mueller |
| 3,856,051 A | 12/1974 | Bain |
| 3,858,615 A * | 1/1975 | Weigl .......................... 138/121 |
| 4,000,341 A * | 12/1976 | Matson ........................ 428/36.9 |
| 4,078,692 A | 3/1978 | Stein |
| 4,196,031 A | 4/1980 | Lalikos et al. |
| 4,316,458 A * | 2/1982 | Hammerton-Fraser .. 128/205.24 |
| 4,463,755 A * | 8/1984 | Suzuki ..................... 128/204.18 |
| 4,653,542 A | 3/1987 | Tascher |
| 4,685,456 A | 8/1987 | Smart |
| 4,838,258 A * | 6/1989 | Dryden et al. .......... 128/204.18 |
| 4,915,104 A | 4/1990 | Marcy |
| 4,923,083 A | 5/1990 | Forbes |
| 4,944,310 A | 7/1990 | Sullivan |
| 5,244,464 A | 9/1993 | Madden et al. |
| 5,400,776 A | 3/1995 | Bartholomew |
| 5,492,151 A | 2/1996 | Wood et al. |
| 5,600,752 A | 2/1997 | Lopatinsky |
| 5,735,266 A | 4/1998 | Smith |
| 6,053,212 A | 4/2000 | Thomas |
| 6,129,082 A | 10/2000 | Leagre |
| 6,286,144 B1 | 9/2001 | Henderson et al. |
| 6,427,727 B1 | 8/2002 | Thomas |
| 6,571,794 B1* | 6/2003 | Hansen .................... 128/204.18 |
| 6,575,165 B1 | 6/2003 | Cook et al. |
| 6,666,209 B2 | 12/2003 | Bennett et al. |
| 6,668,388 B2 | 12/2003 | Buttigieg |
| 6,796,304 B2 | 9/2004 | Odell et al. |
| 6,837,239 B2 | 1/2005 | Beizndtsson et al. |
| 6,889,688 B1 | 5/2005 | Wright |
| 6,948,527 B2 | 9/2005 | Ragner et al. |
| 7,000,611 B2* | 2/2006 | Klemperer .............. 128/204.18 |
| 7,061,832 B1 | 6/2006 | Lansing |
| 7,082,944 B2 | 8/2006 | Gossweiler |
| 7,156,127 B2* | 1/2007 | Moulton et al. ............. 138/122 |
| 8,028,692 B2* | 10/2011 | Ho .......................... 128/200.24 |
| 2002/0189914 A1* | 12/2002 | Naples et al. ........... 188/322.15 |
| 2003/0098084 A1 | 5/2003 | Ragner et al. |
| 2003/0111076 A1 | 6/2003 | Baker |
| 2003/0111126 A1 | 6/2003 | Moulton et al. |
| 2004/0102731 A1* | 5/2004 | Blackhurst et al. ............ 604/26 |
| 2004/0182395 A1 | 9/2004 | Brookman |
| 2004/0200921 A1 | 10/2004 | Chapman et al. |
| 2005/0022817 A1 | 2/2005 | Alvey |
| 2005/0092329 A1 | 5/2005 | Sta-Maria |
| 2005/0126565 A1 | 6/2005 | Huang |
| 2005/0165366 A1 | 7/2005 | Brustad et al. |
| 2006/0070679 A1 | 4/2006 | Ragner |
| 2006/0231100 A1 | 10/2006 | Walker et al. |
| 2007/0175480 A1* | 8/2007 | Gradon et al. ........... 128/207.11 |
| 2007/0267012 A1* | 11/2007 | McCarthy ................ 128/201.11 |
| 2008/0060649 A1* | 3/2008 | Veliss et al. ............. 128/205.25 |
| 2008/0099023 A1* | 5/2008 | Berthon-Jones ......... 128/206.24 |
| 2008/0282495 A1* | 11/2008 | Battle et al. ..................... 15/323 |
| 2009/0065005 A1* | 3/2009 | Ades ....................... 128/205.25 |

FOREIGN PATENT DOCUMENTS

| | | |
|---|---|---|
| CN | 2275174 Y | 2/1998 |
| CN | 1248154 A | 3/2000 |
| CN | 1589167 | 3/2005 |
| CN | 2785622 Y | 6/2006 |
| CN | 1909942 | 2/2007 |
| CN | 1988930 | 6/2007 |
| CN | 101102805 | 9/2008 |
| DE | 702 098 | 1/1941 |
| DE | 882 185 | 7/1953 |
| DE | 199 54 724 A1 | 6/2001 |
| EP | 0 821 978 A2 | 2/1998 |
| EP | 1 075 848 A2 | 2/2001 |
| GB | 933172 | 8/1963 |
| GB | 1 419 841 | 12/1975 |
| JP | 51-129921 | 11/1976 |
| JP | 3-234995 A | 10/1991 |
| JP | 4-67940 A | 3/1992 |
| JP | 2001-79091 A | 3/2001 |
| JP | 2005-503869 A | 2/2005 |
| JP | 2007-524480 A | 8/2007 |
| JP | 2008-537902 A | 10/2008 |
| WO | WO 89/02761 A1 | 4/1989 |
| WO | WO 98/36687 A1 | 8/1998 |
| WO | WO 02/32492 A2 | 4/2002 |
| WO | WO 03/026721 A2 | 4/2003 |
| WO | WO 03/046427 A1 | 6/2003 |
| WO | WO 2005/072806 A2 | 8/2005 |
| WO | WO 2006/113203 A1 | 10/2006 |

OTHER PUBLICATIONS

VACUFLEX GmbH, "VACUFLEX® Thermoplastic Hoses, Ducting & Assemblies," A Schauenburg Hose Technology Company, 6 pages, Jan. 2009.
European Office Action dated May 10, 2011 in European Application No. 08 164 639.0 (5 pages).
Examiner's Report No. 2 dated Nov. 30, 2010 in Australian Application No. 2008221506 (3 pages).
VACUFLEX Gmbh, "New VACUFLEX®—Polyurethane Stretch Hose for Vacuum Cleaners and Hair Dryers," (1 page).
Notification of First Office Action dated Mar. 30, 2012 in Chinese Appln. No. 200810173773.4 with English translation (8 pages).
Extended European Search Report dated Mar. 8, 2012 in European Appln. No. 11186207.4 (7 pages).
Communication dated Jun. 5, 2013 in European Application No. 11 186 207.4 (7 pages).
Notification of the Second Office Action dated Dec. 17, 2012 in Chinese Application No. 200810173773.4, with English Translation (20 pages).
Notice of Reasons for Rejection dated Jan. 15, 2013 in Japanese Application No. 2008-241698, with English Translation (10 pages).
Notification of the Third Office Action dated Jul. 5, 2013 in Chinese Application No. 200810173773.4, with English Translation (16 pages).
Decision of Rejection dated Dec. 17, 2013 in Japanese Application No. 2008-241698, with English Translation (4 pages).
Chinese Office Action dated Jan. 20, 2014 in Chinese Application No. 200810173773.4, with English Translation (11 pages).
European Communication dated Apr. 7, 2014 in European Application No. 11 186 207.4 (5 pages).
Notice of Reasons for Rejection dated Mar. 16, 2015 issued in Japanese Application No. 2014-085716 with English translation (7 pages).
Notice of Reasons for Rejection dated May 11, 2015 issued in Japanese Application No. 2008-241698 with English translation (6 pages).
Decision of Rejection dated Aug. 3, 2015 issued in Chinese Application No. 200810173773.4 with English translation (19 pages).
Notification of the First Office Action dated Jan. 4, 2016 issued in Chinese Application No. 201410532767.9 with English language translation (28 pages).
Notification of the Second Office Action dated Jul. 14, 2016 issued in Chinese Application No. 201410532767.9 with English translation (22 pages).
Notification of Reexamination dated Nov. 21, 2016 issued in Chinese Application No. 200810173773.4 with English translation (13 pages).
Decision of Reexamination dated Feb. 27, 2017 issued in Chinese Application No. 200810173773.4 with English translation (23 pages).
Notification of Reexamination dated Dec. 18, 2017 issued in Chinese Application No. 201410532767.9 with English translation (21 pages).
Notification of the Fifth Office Action dated Feb. 28, 2015 issued in Chinese Application No. 200810173773.4 with English-language translation (17 pages).
Decision of Rejection dated Jun. 5, 2014 in Chinese Application No. 200810173773.4 (10 pages).

(56) References Cited

OTHER PUBLICATIONS

Decision of Reexamination dated Apr. 20, 2018 issued in Chinese Application No. 201410532767.9 with English translation (35 pages).

* cited by examiner

RETRACTABLE TUBE FOR CPAP

CROSS REFERENCE TO RELATED APPLICATIONS

This application claims priority to U.S. Applications 60/973,902, filed Sep. 20, 2007, 60/987,825, filed Nov. 14, 2007, and 61/031,407, filed Feb. 26, 2008, the entire contents of each incorporated herein by reference.

FIELD OF THE INVENTION

The present invention relates to a retractable tube for use in Continuous Positive Airway Pressure (CPAP) therapy used to treat, for example, Sleep Disordered Breathing (SDB), such as Obstructive Sleep Apnea (OSA).

BACKGROUND OF THE INVENTION

The application of Continuous Positive Airway Pressure (CPAP) for therapy of Obstructive Sleep Apnea (OSA) was first taught by Sullivan in U.S. Pat. No. 4,944,310. In CPAP treatment of OSA, pressurized air or other breathable gas is provided to the entrance of a patients' airways at a pressure elevated above atmospheric pressure, for example in the range of 4 to 30 cm $H_2O$ to "splint" open the patients' airways and prevent obstructive apneas. Apparatus to deliver CPAP therapy typically comprise a blower, or flow generator, an air delivery conduit, hose or tube, and a patient interface, for example a mask.

In order to deliver effective therapy, a substantially leak proof seal should be maintained between the patient interface and the face of the patient. Undesirable forces applied to the mask, for example, tube drag or the weight of the mask, or components attached to the mask, tend to disrupt the seal formed between the patient interface and the patient.

Various solutions have been proposed for reducing the undesirable forces that may be applied to a mask, including tube drag. Some of these solutions include a rotating or swiveling elbow to connect the air delivery hose and the patient interface. The rotating or swiveling elbow allows some form of rotation before the tube pulls on the patient interface and disrupts the seal. Some prior art swivel and elbow arrangements use tight tolerances, which might result in friction in the movement of the swivel elbow, thus reducing the mobility and flexibility of the elbow swivel joint.

Another solution which has been proposed to reduce the application of undesirable forces on the patient interface is a headgear to provide stability to the patient interface and maintain the seal during the application of the forces, including tube drag. The headgear assembly may be designed such that the stabilizing straps are provided at an angle with respect to the patient interface and the face of the patient to counteract the undesirable forces, including tube drag. In one known mask assembly, the headgear includes a cap portion with four straps. In use, the cap portion engages the back of the patient's head and two lower straps extend between the cap portion and a nasal mask while the two upper straps extend between the cap portion and a forehead support. Such headgear assemblies may be uncomfortable for the patient and difficult to adjust to obtain a substantially leak proof seal.

Another solution for offsetting tube drag and other undesirable forces on the patient interface include clips that connect the air delivery conduit or hose to the patient's clothing, such as the patient's pajamas. Clips have also been used to connect the air delivery conduit or hose to a stationary object, such as the patient's bed, to remove or reduce tube drag affecting the mask seal.

It has also been proposed to provide a short tube between the air delivery conduit or hose to provide extra flexibility and rotation to the air delivery conduit or hose before the tube pulls on the mask.

SUMMARY OF THE INVENTION

One aspect of the invention relates to a retractable tube for use in a CPAP apparatus that reduces, or eliminates, the application of tube drag forces on the patient interface.

Another aspect of the invention relates to a retractable tube for use in a CPAP apparatus that reduces tangling of the air delivery hose or conduit.

Still another aspect of the invention relates to a retractable tube for use in a CPAP apparatus that reduces the weight and/or bulk of the retractable tube.

Yet another aspect of the invention relates to a retractable tube for use in a CPAP apparatus that is formed of biocompatible material and can be cleaned and disinfected numerous times.

A further aspect of the invention relates to a retractable tube for use in a CPAP apparatus that permits a headgear to maintain a seal between the patient interface and the patient's face using less straps and/or straps of reduced elastic force.

According to a sample embodiment of the invention, a retractable tube for use in a respiratory apparatus for delivering a pressurized flow of breathable gas to a patient tube has an internal diameter of about 30 mm or less, a weight of about 500 g/m or less, and an unextended length of about 2 m or less. The retractable tube comprises a portion that is extensible in a range of about 1:1-1:4 in response to force applied to the tube, and the extensible portion is configured to return the tube to its unextended length in the absence of force, or reduced force, applied to the tube.

According to another sample embodiment of the invention, a retractable tube for use in a respiratory apparatus for delivering a pressurized flow of breathable gas to a patient has an internal diameter of about 30 mm or less, a weight of about 500 g/m or less, and an unextended length of about 2 m or less. The retractable tube comprises a portion that is extensible in a range of about 1:1-1:2 in response to force applied to the tube, and the extensible portion is configured to return the tube to its unextended length in the absence of force, or reduced force, applied to the tube. The retractable tube has a spring constant of about 25 N/m or less, According to a further sample embodiment of the invention, a method of delivering a flow of pressurized breathable gas from a flow generator configured to generate the pressurized flow of breathable gas to a patient interface configured to engage a patient's face and deliver the pressurized flow of breathable gas to the patient's airways comprises connecting the flow generator and the patient interface using a retractable hose.

According to an even further sample embodiment of the invention, a respiratory apparatus for delivering a flow of pressurized breathable gas to a patient comprises a flow generator configured to generate the pressurized flow of breathable gas; a patient interface configured to engage the patient's face and deliver the pressurized flow of breathable gas to the patient's airways; and a retractable tube to connect the flow generator and the patient interface.

According to still another sample embodiment of the invention, a mask system comprises a patient interface; and a retractable tube provided to the patient interface.

According to yet another sample embodiment of the invention, a mask system for a patient comprises a patient interface; a tube provided to the patient interface; and means for maintaining a low profile of the tube according to positioning of the patient.

According to a further sample embodiment of the invention, a retractable tube comprises a plurality of ring-shaped elements; and an elastic member connected to each of the ring-shaped elements.

Other aspects, features, and advantages of the inventions will become apparent from the following detailed description when taken in conjunction with the accompanying drawings, which are a part of this disclosure and which illustrate, by way of example, principles of the inventions.

BRIEF DESCRIPTION OF THE DRAWINGS

The accompanying drawings facilitate an understanding of the various embodiments of this invention. In such drawings:

FIGS. 7a and 7b schematically depict a retractable tube for CPAP according to a sample embodiment of the invention, wherein FIG. 7A depicts the retractable tube in an extended configuration and FIG. 7B depicts the retractable tube in a neutral configuration;

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

First Retractable Tube Embodiment

Figure 1:
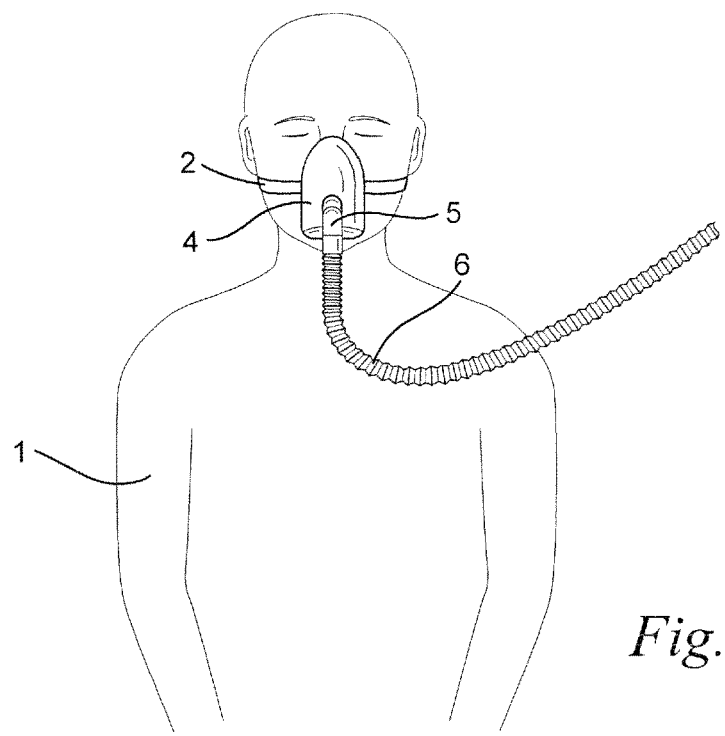
FIG. 1 schematically illustrates an arrangement for CPAP using a retractable tube according to a sample embodiment of the invention.

Referring to FIG. 1, a patient interface 4, for example a mask, is secured to a patient 1 by a headgear assembly 2. A flow of pressurized breathable gas is delivered to the patient interface 4 by a retractable tube 6. As discussed in more detail below, the retractable tube 6 is extensible and retractable (e.g. by compression) to accommodate movement of the patient 1, for example movement of the patient's head. The retractable tube 6 may be attached to the patient interface 4 using a swivel elbow assembly 5. The retractable tube 6 may be of sufficient length to accommodate some movement of the patient's head without extension or retraction of the tube 6.

Second Retractable Tube Embodiment

Figure 2:
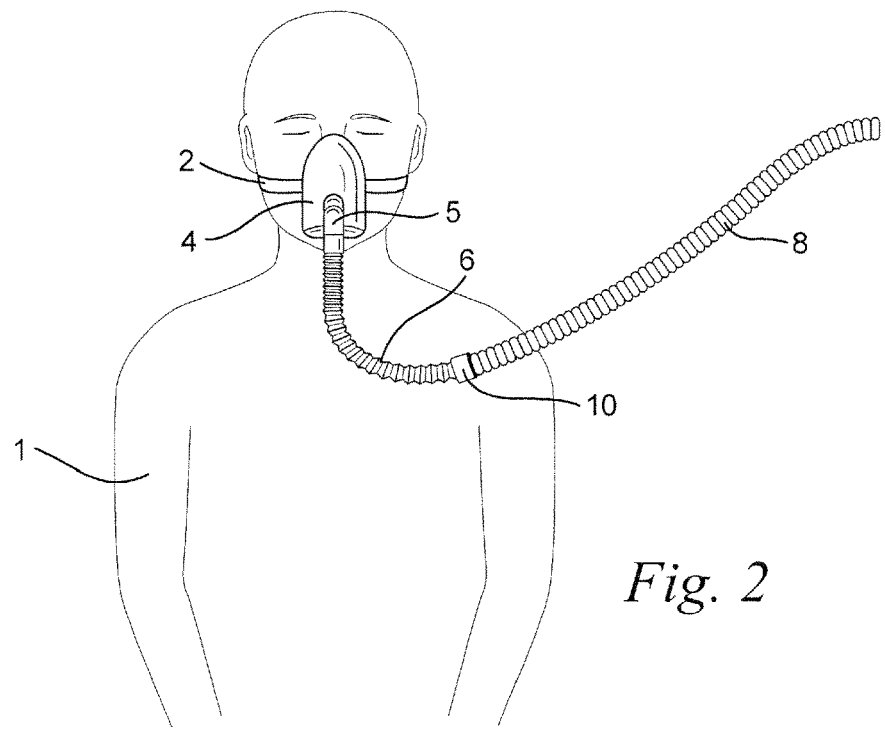
FIG. 2 schematically illustrates an arrangement for CPAP using a retractable tube according to another sample embodiment of the invention.

According to another sample embodiment of the invention shown in FIG. 2, the retractable tube 6 may be connected to a non-retractable tube 8 by a connector, or cuff, 10. The retractable tube 6 may be connected to the patient interface 4 by a swivel elbow assembly 5. In the sample embodiment shown in FIG. 2, the non-retractable tube 8 may be anchored to a fixed object, for example the patient's bed or a table, to prevent tube drag. The retractable tube 6 may extend or compress to accommodate movement of the patient, for example movement of the patient's head. The combined length of the retractable tube 6 and the non-retractable tube 8 may be sufficient to accommodate some movement of the patient's head without extension or retraction of the retractable tube 6. Alternatively, the length of the retractable tube 6 may alone be sufficient to accommodate some movement of the patient's head without extension or retraction of the retractable tube 6.

It should be appreciated that the tube may also be integrally formed to include a non-retractable section and a retractable section. Such a tube would have an adjustable length, but fixed minimum and maximum lengths. An example of such a configuration would be similar to a flexible drinking straw.

It should also be appreciated that the retractable tube 6 may be connected in series to other retractable tubes. Other such retractable may vary in flexibility so as to tailor the flexibility of the tubing system. Other such retractable tubes may also vary in length to the first retractable tube.

Retractable Tube, Connector and Strap

Figure 3:
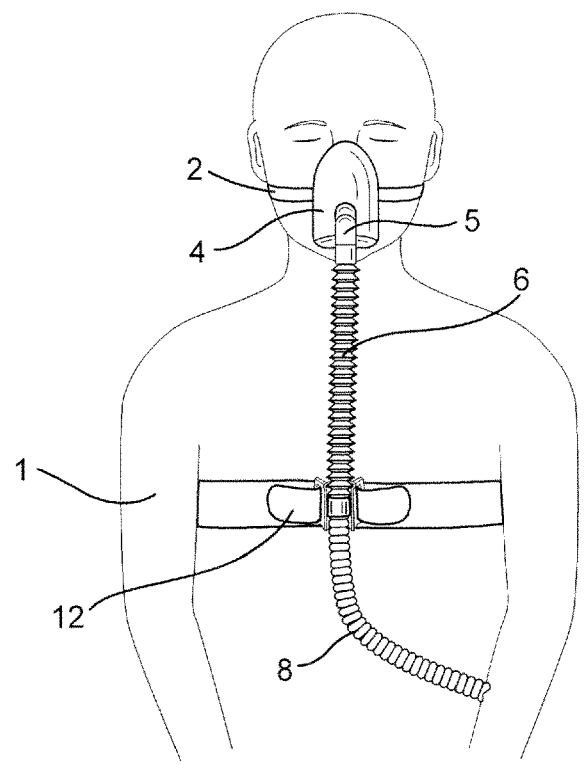
FIGS. 3 and 4 schematically illustrate an arrangement for CPAP using a retractable tube according to another sample embodiment of the invention.

As shown in FIG. 3, the retractable tube 6 may be connected to the non-retractable tube 8 at a chest strap 12, e.g. an elastic strap, that is strapped around the patient's torso. Although the strap 12 is shown as strapped around the patient's torso, it should be appreciated that the strap may also be encircled around, for example, an arm or the neck of the patient. It should also be appreciated that the strap may be secured to an object other than the patient, for example a table or a bed post.

Figure 4:
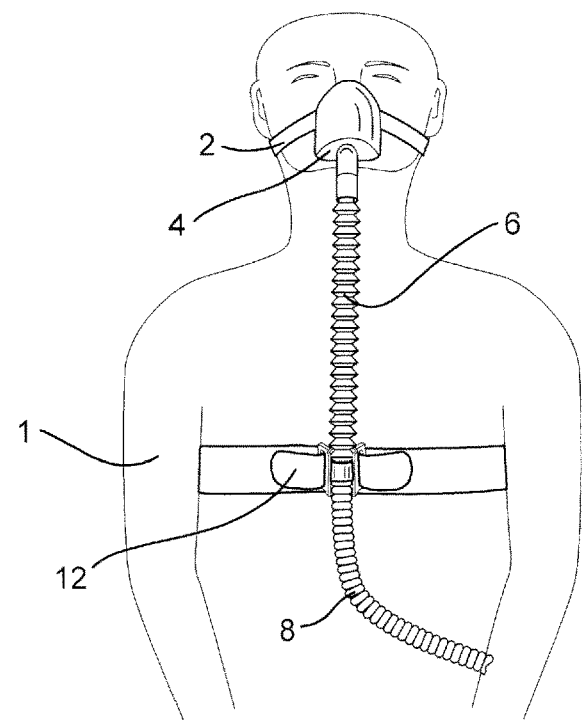

Referring to FIG. 4, movement of the patient, for example movement of the patient's head, may be accommodated by the retractable tube 6 by extension of the retractable tube 6 from the position shown in FIG. 3 to the position shown in FIG. 4. Although the movement of the patient's head from the position in FIG. 3 to the position in FIG. 4 is generally in the tilting, or nodding, direction, it should be appreciated that the retractable tube 6 may also accommodate movement and turning of the patient's head in a side, i.e. left-to-right, direction.

First Strap and Connector Embodiment

Figure 5:
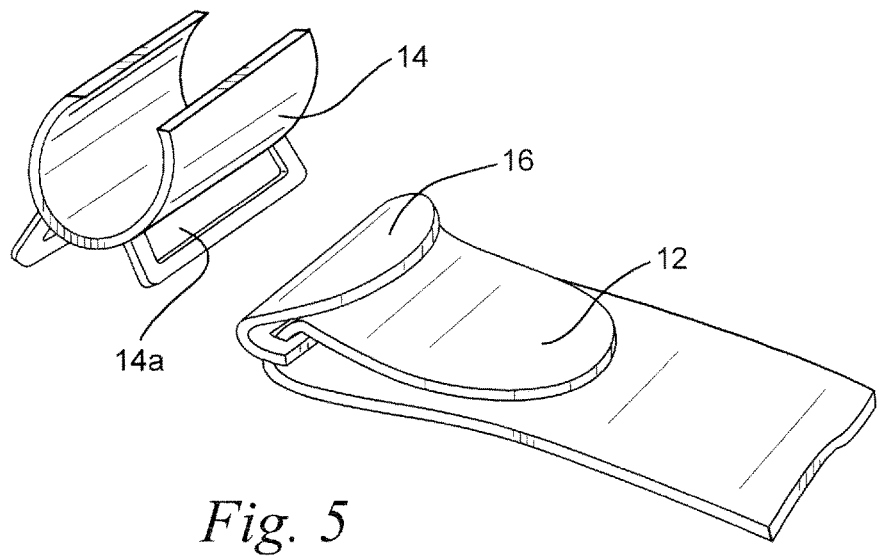
FIG. 5 schematically illustrates an arrangement for securing a retractable tube according to a sample embodiment of the invention.

Referring to FIG. 5, the strap 12 may be attached to a C-shaped tube retainer 14 by a curved hooking plate 16. The C-shaped tube retainer 14 is configured to receive the retractable tube 6 and the non-retractable tube 8 connected by the connector, or cuff, 10. The C-shaped tube retainer 14 is configured to clamp the retractable tube 6, the cuff 10, and the non-retractable tube 8 to maintain the connection between the retractable tube 6 and the non-retractable tube 8. The curved hooking plate 16 is configured to engage a slot 14a of the C-shaped tube retainer 14 to permit the strap 12 to be quickly clipped to and released from the C-shaped tube retainer 14. The strap 12 may include hook and loop fastener portions to hold the curved hooking plate 16. For example, the end of the strap 12 may have hooks that engage loops formed on the remainder of the strap 12, or vice versa, to permit the strap 12 to be looped through the curved hooking plate 16 and the end of the strap 12 fastened to the remainder of the strap 12.

Second Strap and Connector Embodiment

Figure 6:
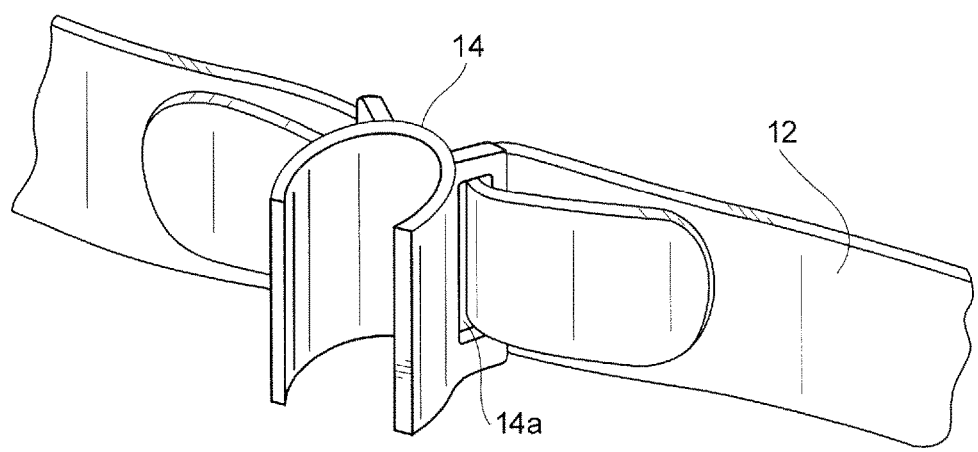
FIG. 6 schematically illustrates an arrangement for securing a retractable tube according to another sample embodiment of the invention.

According to another sample embodiment shown in FIG. 6, the strap 12 is looped through the slot 14a of the C-shaped tube retainer 14. The C-shaped tube retainer 14 is configured to clamp the retractable tube 6, the connector 10 and the non-retractable tube 8 to maintain the connection. The strap 12 may include hook and loop fasteners, in a manner similar to that discussed above with respect to FIG. 5, to secure the C-shaped tube retainer 14 to the strap 12.

Third Retractable Tube Embodiment

Figure 7A:
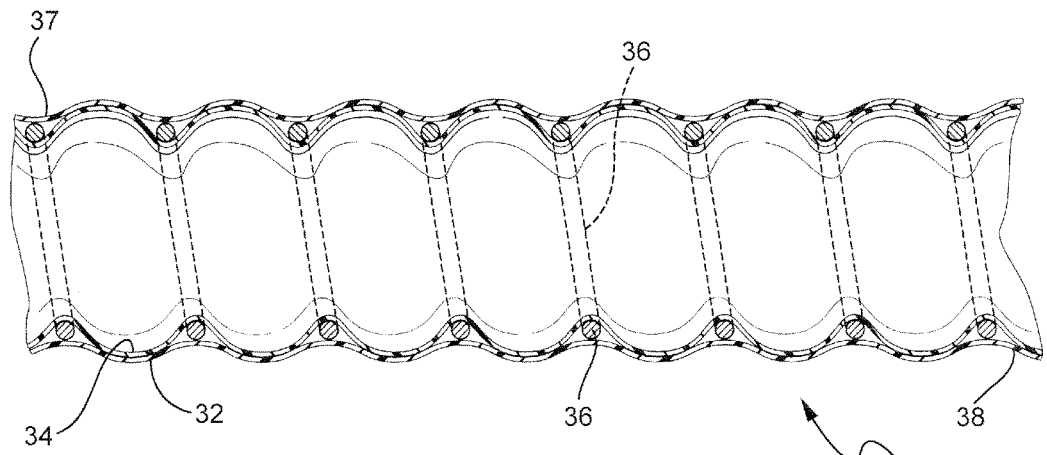
Figure 7B:
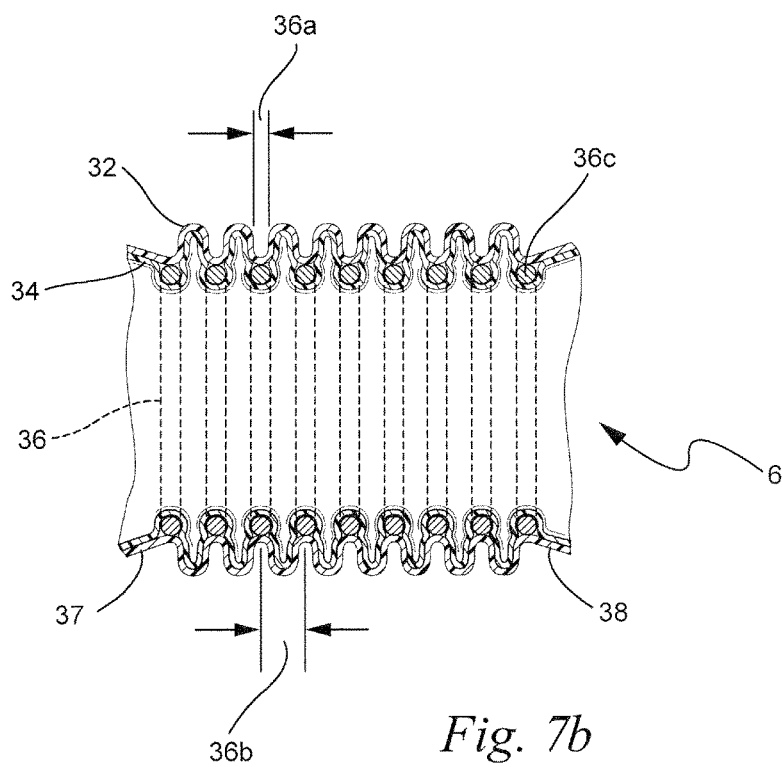

Referring to FIGS. 7a and 7b, a retractable tube 6 according to a sample embodiment of the invention may comprise a spring 36 that biases the tube 6 toward a retracted, or neutral, state, shown in FIG. 7b. The spring 36 may be integrated with the body of the tube 6 or can be internal or external to the body of the tube 6. The spring 36 may be a helical spring that extends along the full length of the tube 6, but it may also be comprised of multiple spring coils and/or multiple diameter spring coils. The spring(s) may thus provide a variable retraction force. As another example, the spring(s) may be formed of a magnetic material so that adjacent coils are attracted to, or repulsed by, one another.

As shown in FIG. 7b, the spring 36 may be formed of a helically wound strand 36c. The strand 36c may be a metallic wire. It should be appreciated that the strand 36c may be formed of material other than metal, for example the strand 36c may be formed of a plastic material. The diameter 36a of the strand 36c may affect the spring constant of the spring 36 and the retractable tube 6. As the diameter 36a of the strand 36c increases, the force required to elongate the spring 36 increases. The diameter 36a of the strand 36c may be, for example, between about 0.1 mm to 5 mm, for example about 1 mm-4 mm, for example about 1.5 mm-2.5 mm, for example about 2 mm. It should be appreciated that the strand diameter 36a may vary along the length of the spring 36 to provide a varying spring constant. It should further be appreciated that the cross section of the strand 36c need not be circular as shown in FIGS. 7a and 7b and that the strand 36c may have any cross section, e.g. polygonal.

The pitch 36b of the spring 36 may affect the maximum elongation of the retractable tube spring 36 and the retractable tube 6. Generally speaking, the larger the pitch 36b, the larger the maximum elongation of the retractable tube 6 may be. The pitch 36b of the spring 36 may be, for example, between about 2 mm-9 mm, for example about 3 mm-6 mm, for example about 4.8 mm. It should be appreciated that the pitch 36b of the spring 36 may vary along the length of the spring 36 to provide sections of the retractable tube 6 with different elongations.

As shown in FIGS. 7a and 7b, the spring 36 may be integrated within the tube 6. The spring 36 may be covered with a cover material 32 on the outside of the tube 6 and a cover material 34 on the inside of the tube 6. The cover materials 32, 34 provide a flexible elongated body for the tube 6. The cover material 32 and/or 34 may be molded onto the spring 36 or wound with interlocking strips onto the spring 36.

The spring 36 may not be attached to the tube 6, but may be positioned around the exterior of the hose 6, or positioned within the tube 6. In other words, the tube 6 may comprise a single cover material and the spring 36 may be provided on the outside of the cover material in an exposed state, or may be provided on the inside of the cover material and exposed to the flow of pressurized breathable gas. The spring 36 may extend substantially the full length of the retractable tube 6, i.e. from one end 37 to the other end 38. It should be appreciated that the spring 36 may be provided along less than substantially the entire length of the retractable tube, or that multiple springs may be provided intermediate the ends, or multiple springs may be provided along substantially the entire length of the retractable tube 6. The ends 37, 38 of the retractable tube 6 may be configured to connection to a swivel elbow assembly of a mask, an outlet of a flow generator, or an inlet or outlet of a humidifier. In general, the ends 37, 38 of the retractable tube 6 may be configured for connection to any component of a CPAP apparatus, or component usable with a CPAP apparatus.

The cover material, or materials, may be bowed outwardly and/or inwardly between coils of the spring 36 to provide the cover material(s) with room to move out of the way when the retractable tube 6 retracts and the coils of the spring 36 move closer together.

The cover materials 32, 34 may be formed of biocompatible materials that are capable of being used in the air path of the CPAP apparatus. The biocompatible material used to form the cover materials should be able to be disinfected to be used multiple times and for multiple patients. The cover materials 32, 34 may be plastic or silicone or thermoplastic urethane (TPU) or combinations thereof, and in the case of exposure to the air path, the cover materials may be formed of biocompatible materials that are capable of being used in the air path of the CPAP apparatus.

The spring 36 may be formed of metal or plastic, and in the case of exposure to the air path, the spring may be formed of biocompatible material(s) capable of being used in the air path of the CPAP apparatus.

As the tube 6 may be used as a pressure tube in a CPAP apparatus, the spring 36 is configured to have a bias that exerts a retracting force on the cover materials 32, 34. The spring 36 may be configured so that the spring continues to apply the retracting force even when the tube 6 is in its fully retracted state. Spring 36 thus may be a coiled spring that still provides retracting force even when fully retracted. From the natural retracted state, the spring 36 is stretched before the cover materials 32, 34 are placed onto it. When the spring 36 is released, the tube naturally takes on its fully retracted, or neutral, state.

The material used for the retractable tube 6 may affect it spring characteristics. For example, the material used for spring 36 may have a tensile modulus of about 150-250 MPa, for example about 160-240 MPa, as another example about 160-220 MPa, as a further example about 180-200 MPa, as a still further example about 180 MPa, and as an even further example about 188 MPa. The spring 36 may be formed of, for example, polyester elastomer, such as HYTREL® 5556 or 5526 from DuPont.

The spring 36 and the connector, or cuff, 10 may be made from the same material to improve manufacturing efficiency, for example, by thermally forming the spring and connector/cuff.

Fourth Retractable Tube Embodiment

Figure 8:
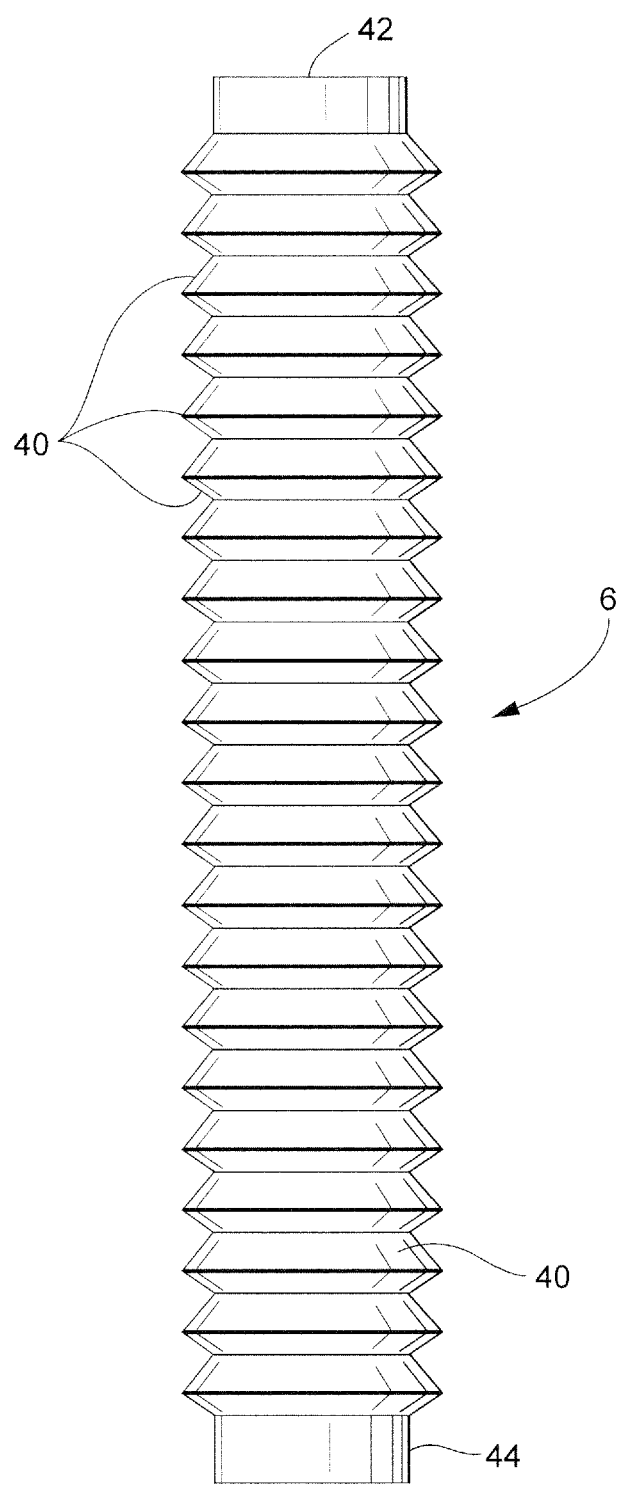
FIG. 8 schematically depicts a retractable tube for CPAP according to another sample embodiment of the invention.

Referring to FIG. 8, a retractable tube 6 according to another sample embodiment of the invention comprises a plurality of bellows 40 which may or may not be spring biased into the retracted position. The bellows may also be magnetically attracted to, or repulsed by, one another. The retractable tube 6 may be formed of a plastic material by, for example, molding. The retractable tube 6 may include end portions 42, 44 that are configured for connection with a swivel elbow assembly connected to the patient interface, the connector, or cuff, 10 for connection to the non-retractable tube 8, or for connection to a flow generator configured to supply a flow of pressurized breathable gas, or any other component of a CPAP apparatus, or apparatus usable with a CPAP apparatus, for example a humidifier.

Fifth Retractable Tube Embodiment

Figure 9A:
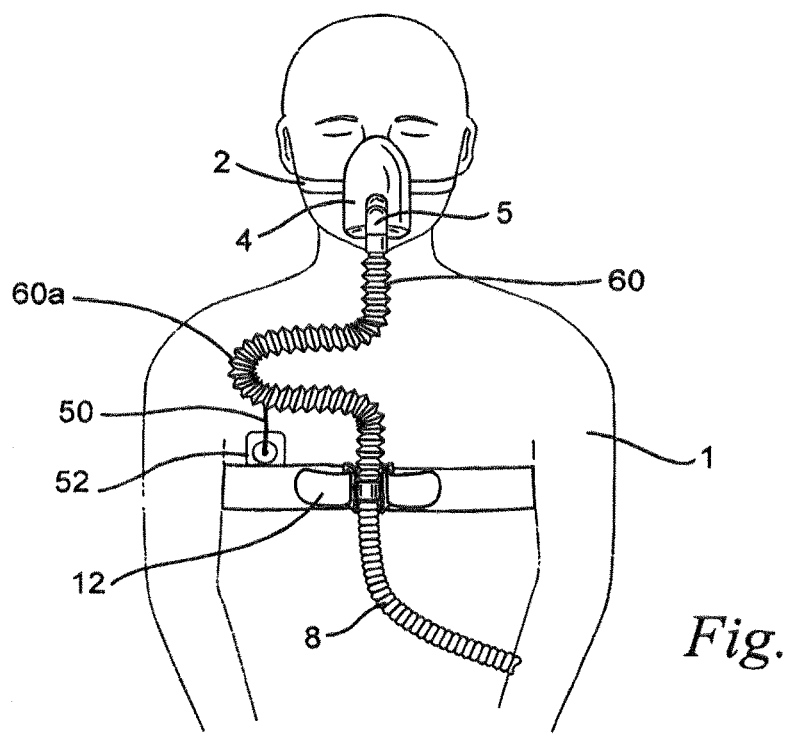
FIGS. 9a and 9b schematically illustrate an arrangement for CPAP using a retractable tube according to another sample embodiment of the invention.
Figure 9B:
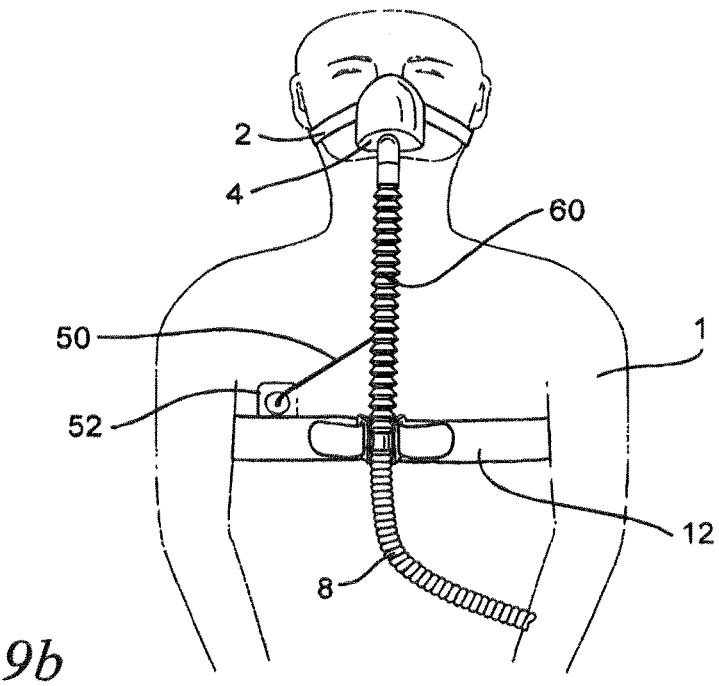

As shown in FIGS. 9a and 9b, a retractable tube 60 according to another sample embodiment of the invention may include a loop portion 60a. The retractable tube 60 may also include a spring or bellows configuration as described above. In its neutral, or relaxed, shape, the loop portion 60a of the retractable tube 60 may extend between the strap 12 and the swivel elbow assembly 5. An extensible cord 50 may extend from the strap 12 to the loop portion 60a of the retractable tube 60. The cord 50 may be spring biased to a retracted position, like a seat belt. Although the extensible cord 50 is shown in FIGS. 9a and 9b as being attached to a lower portion of the loop portion 60a of the retractable tube 60, it should be appreciated that the cord 50 may be attached to the loop portion 60a at any location.

The extensible cord 50 may be connected to the strap 12 by a winding mechanism 52. The winding mechanism 52 may be a spring biased winding mechanism, e.g. similar to a seat belt retractor mechanism, that is configured to wind the cord 50 around a spool or reel contained in the winding mechanism 52. When the patient's head moves, for example as shown in FIG. 9b, the loop portion 60a of the retractable tube 60 straightens out and the cord 50 extends from the winding mechanism 52 to accommodate the movement, i.e. straightening, of the loop portion 60a. When the patient's head moves back to the position shown in FIG. 9A, the winding mechanism 52 retracts the cord 50 to assist the loop portion 60a in returning to its relaxed state.

Figure 17:
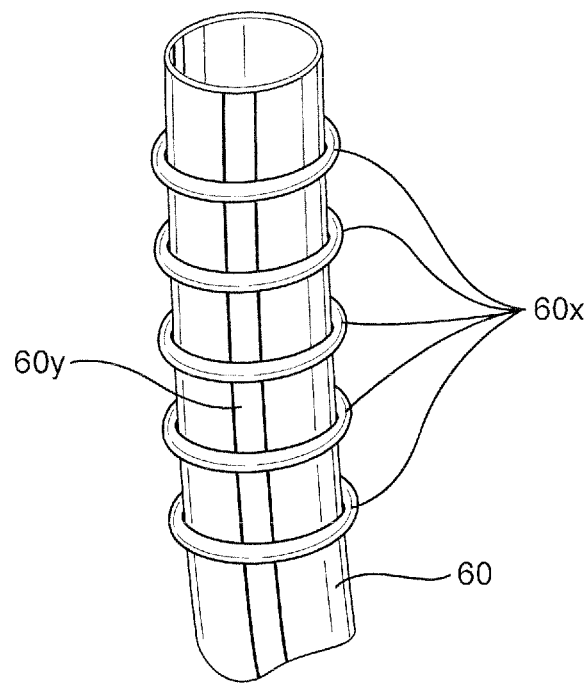
FIG. 17 schematically illustrates a retractable tube according to another sample embodiment of the invention.

According to another sample embodiment of the invention shown in FIG. 17, the retractable tube 60 may include a plurality of connecting rings 60X connected by an elastic member 60Y extending along the tube.

Providing the retractable tube in connection with the swivel elbow of the patient interface reduces, or eliminates, the force of tube drag applied to the patient interface which reduces, or eliminates, a major component of force applied to the patient interface. This allows the design of the CPAP apparatus to focus on supporting the weight of the patient interface to maintain a substantially leak proof seal. The requirements for supporting the weight of the patient interface to maintain a substantially leak proof seal are much less than the forces contributed by tube drag. In addition, the design of the CPAP apparatus may balance the force from the retractable tube against the tension of the headgear necessary to maintain a substantially leak proof seal.

Figure 10:
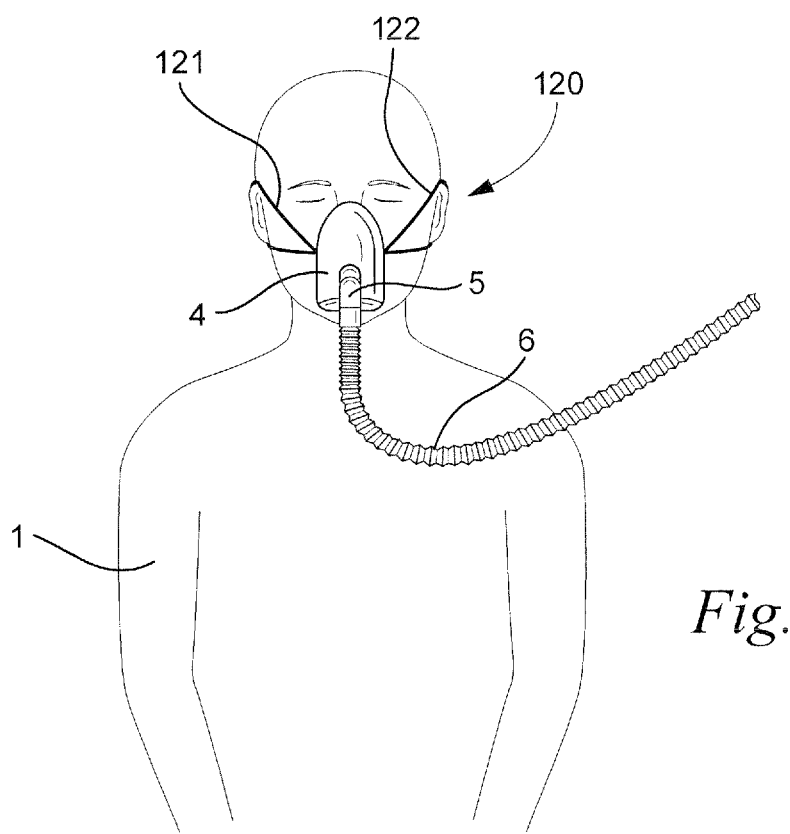
FIG. 10 schematically illustrates an arrangement for CPAP that includes a retractable tube and a headgear that includes straps configured to engage the patient's ears.

Referring to FIG. 10, a CPAP apparatus according to a sample embodiment of the invention may include a headgear 120 that comprises ear engaging straps 121, 122. The use of ear straps provides a less intrusive apparatus that improves patient comfort. Although the headgear including ear straps is shown in FIG. 10 in combination with the retractable tube that is extensible and compressible along its entire length, it should be appreciated that the ear straps may be used as a headgear for any of the sample embodiments disclosed herein.

As shown in FIGS. 2-4, 9a and 9b, the non-retractable tube 8 may have an internal diameter of 22 mm, which may be configured for connection to currently available flow generators/blowers and/or humidifiers. The internal diameter of the retractable tube 6 may have a diameter equal to the non-retractable tube 8, or an internal diameter smaller than the non-retractable tube 8. The connector, or cuff, 10 may be configured to connect the non-retractable tube 8 and the retractable tube 6 in both situations, i.e. in the case where the internal diameters are substantially equal and in the case where the internal diameters are unequal. For example, the cuff 10 may be formed of resilient material that can accommodate tubes of different diameters.

The retractable tube may have a length of up to about 2 m. For example, the retractable tube of FIG. 1 may have a total length not exceeding about 1 m. Alternatively, the total length of the retractable tube and the non-retractable tube may have a length not exceeding about 2 m.

Stretch ratio is the change in the size of the pitch 36b from the relaxed, or neutral state (FIG. 7b) to the expanded state (FIG. 7a). A stretch ratio of the retractable tube should be in a range of about 1:1-1:4. The retractable tube may thus be able to expand from about 0%-400%. However, the retractable tube may also have a stretch ratio between 1:1-1:4, for example about 1:2, or about 2:3. According to one sample embodiment of the invention, the retractable tube may have a stretch ratio between about 5:7-1:2 and be able to increase in length from about 40-100% (±20%). In this sample embodiment, movement of the patient without breaking the seal of the mask is maximized. For example, the retractable tube may be configured to permit the patient's head to tilt all the way from a fully nodding position (i.e. chin touching chest) to a fully tilted position (i.e. head fully back). The retractable tube may also be configured, for example, to permit the patient's head to turn fully from side-to-side (i.e. left to right).

The retractable tube should have a spring constant of about 25 N/m or less, for example, about 7 N/m. The retractable tube may have an internal diameter up to about 30 mm, for example between about 10-20 mm, for example about 12 mm, or as another example about 8 mm. It should be appreciated that the internal diameter of the retractable tube may be determined on the pressure of the flow of breathable gas. For example, the retractable tube may be provided with an internal diameter of about 13.3 mm to deliver a flow of pressurized breathable gas at 12 cm $H_2O$. The weight of the retractable tube may be up to about 500 g/m, for example about 100 g/m or less, or as another example about 50 g/m or less.

The use of the retractable tube reduces the forces applied to the patient interface by tube drag and allows the headgear to use fewer, or no, straps which improves patient comfort. The use of fewer straps for the headgear also improves the stability of the patient interface as fewer straps are available to destabilize the mask.

The retractable tube also reduces tangling of the tube during use and may reduce the size, weight and bulk of the CPAP apparatus by providing a flexible and extensible path for the flow of pressurized breathable gas that may be shorter, smaller, and/or lighter than currently used tubes or hoses. The retractable tube is highly bendable and this is readily apparent by comparison with the tubes of prior art masks.

Referring to FIGS. 11-16, a retractable tube according to a sample embodiment of the invention and three other known tubes were tested and compared. The retractable tube according to the sample embodiment is sample number 4 in the tests described below. The retractable tube of sample number 4 includes a cover material(s) of TPU and a spring formed of ABS. The spring was formed of a strand having a diameter of 2 mm and had a pitch of 4.8 mm. Sample number 1 was a short tube used with ResMed's Swift™ mask. Sample number 2 was a tube used with Sleepnet's IQ® mask and sample number 3 was a tube used with Respironic's Optilife™.

Figure 11:
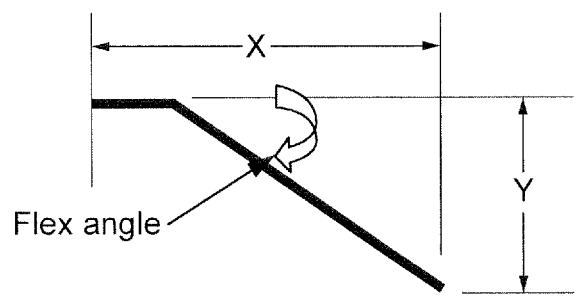
FIG. 11 schematically illustrates a tube bending test arrangement and the displacements measured to determine the angle of displacement.
Figure 12:
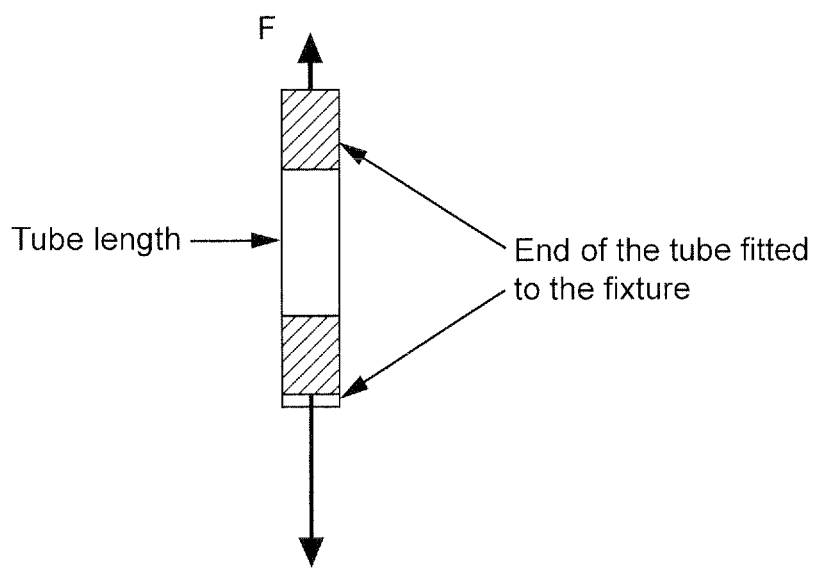
FIG. 12 schematically illustrates a tube testing arrangement used to take the displacement measurements to determine the spring constant of a tube.
Figure 13:
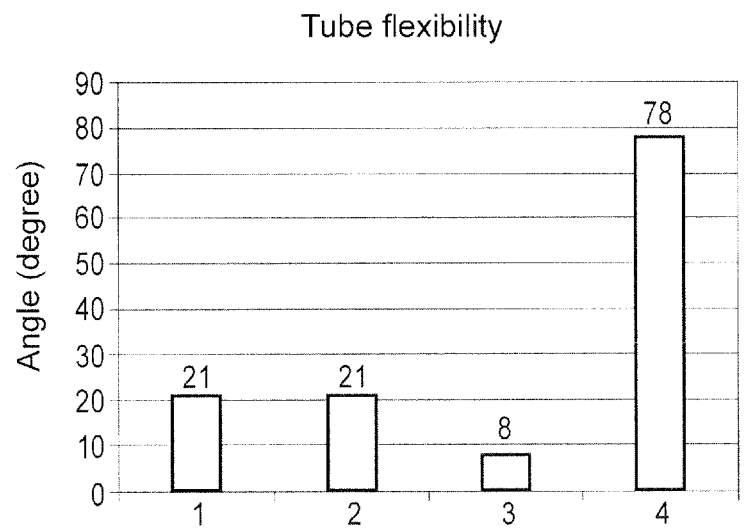
FIG. 13 is a chart of the measured flexibility of the four sample tubes listed in Table 1.

A test was performed to measure tube deflection responsive to an applied force. Each tube was set up in a cantilever arrangement as shown in FIG. 11 and an 8.3 g weight was attached to the free end of the tube. The results are shown below in Table 1.

Table 1 shows that the retractable tube according to the sample embodiment is about three times more bendable than the ResMed's Swift™ tube and Sleepnet's IQ® tube and about ten times more bendable than the Respironic's Optilife™ short tube. For comparison, the results are charted in FIG. 13.

TABLE 2

| Sample number | Tube | Tube dimensions | Stretch ratio |
|---|---|---|---|
| 1 | Swift ™ short tube | 15 mm ID × 300 mm, Flexible type Swift II design (Corrugated) | 1:1 |
| 2 | Sleepnet IQ ® tube | 16.5 mm ID × 255 mm (Corrugated) | 1:3 |
| 3 | Respironics Optilife ™ short tube | 13.5 mm to 20 mm ID × 150 mm, Variable ID tube (Tapered) | 4:5 |
| 4 | TPU/ABS Retractable tube | 13.5 mm ID × 300 mm (Corrugated) | 1:2 |

A stretch ratio of the retractable tube should be in a range of about 1:1-1:4, for example 1:2, or 2:3. The retractable tube may thus be able to increase in length from about 40-100% (±20%) to accommodate movement of the patient, for example head movement. For example, the retractable tube may be configured to permit the patient's head to tilt all the way from a fully nodding position (i.e. chin touching chest) to a fully tilted position (i.e. head fully back). The retractable tube may also be configured, for example, to permit the patient's head to turn fully from side-to-side (i.e. left to right).

Figure 14:
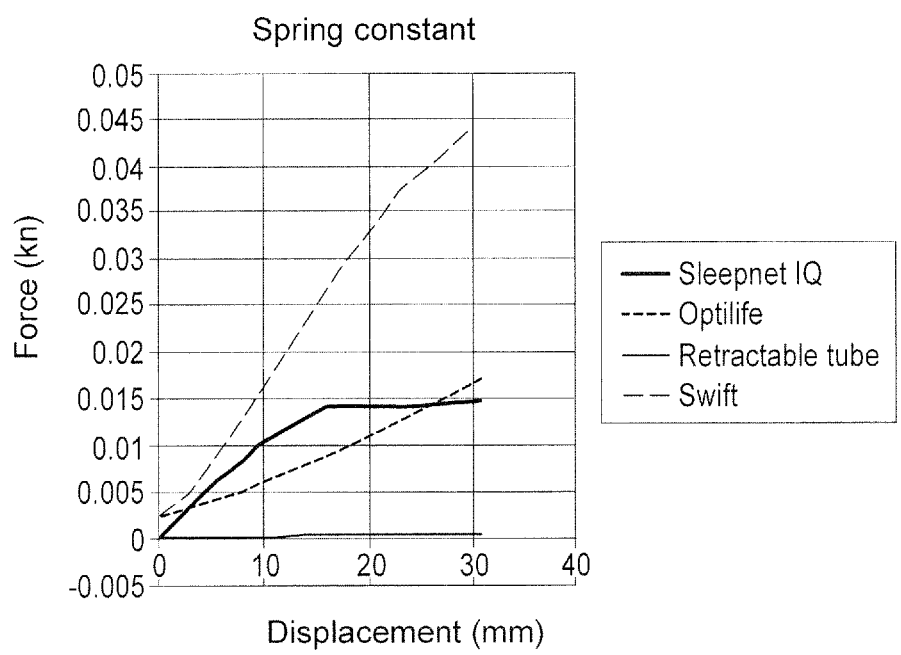
FIG. 14 is a graph of the measured spring constants of the four sample tubes listed in Table 1.
Figure 15:
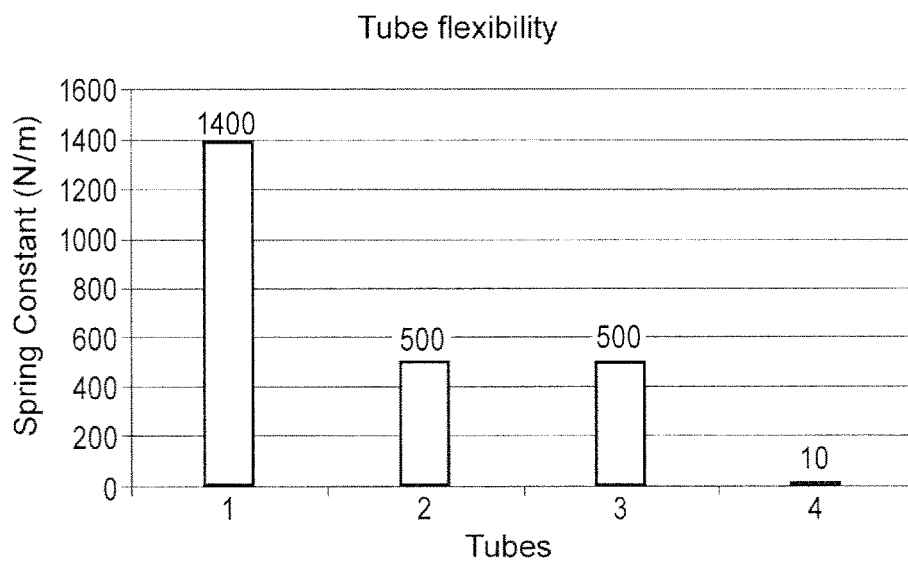
FIG. 15 is a chart of the measured spring constants of the four sample tubes listed in Table 1.

The retractable tube according to the sample embodiment of sample number 4 has a relatively low spring constant compared to the other prior art tubes discussed in Table 1. The spring constants of the tubes were measured using an Instron® machine, schematically illustrated in FIG. 12, and the results are shown in FIG. 14 and a comparison of the results is charted in FIG. 15. FIG. 15 shows that the spring constant of the sample embodiment of the retractable tube (sample number 4) is a factor of 50 less than the spring constant of the Sleepnet's IQ® tube (sample number 2) and the Respironic's Optilife™ short tube (sample number 3) and a factor of 140 less than the ResMed Swift™ short tube (sample number 1).

Although the sample embodiments have been shown and described as including a mask covering the patient's mouth and nose, it should be appreciated that any patient interface may be used, including a mask that covers only the patient's nose, nasal prongs or pillows, an interface comprising cannulae, or an interface that includes a cushion that covers the patient's mouth and includes nasal prongs or pillows connected to the cushion. The patient interface may also comprise a frame and a foam provided to the frame. The patient interface may also comprise the frame and a foam with a cannula seal or nasal prongs provided to the frame.

TABLE 1

| Sample number | Tube | Tube dimensions | Distance X (cm) | Distance Y (cm) | Angle (°) |
|---|---|---|---|---|---|
| 1 | Swift ™ short tube | 15 mm ID × 300 mm, Flexible type Swift design (Corrugated) | 28 | 11 | 21 |
| 2 | Sleepnet IQ ® tube | 16.5 mm ID × 255 mm, Flexible type Swift design (Corrugated) | 23 | 9 | 21 |
| 3 | Respironics Optilife ™ short tube | 13.5 mm to 20 mm ID × 150 mm, Variable ID tube (Tapered) | 15 | 2 | 8 |
| 4 | TPU/ABS Retractable tube | 13.5 mm ID × 300 mm (Corrugated) | 6 | 28 | 78 |

Figure 16:
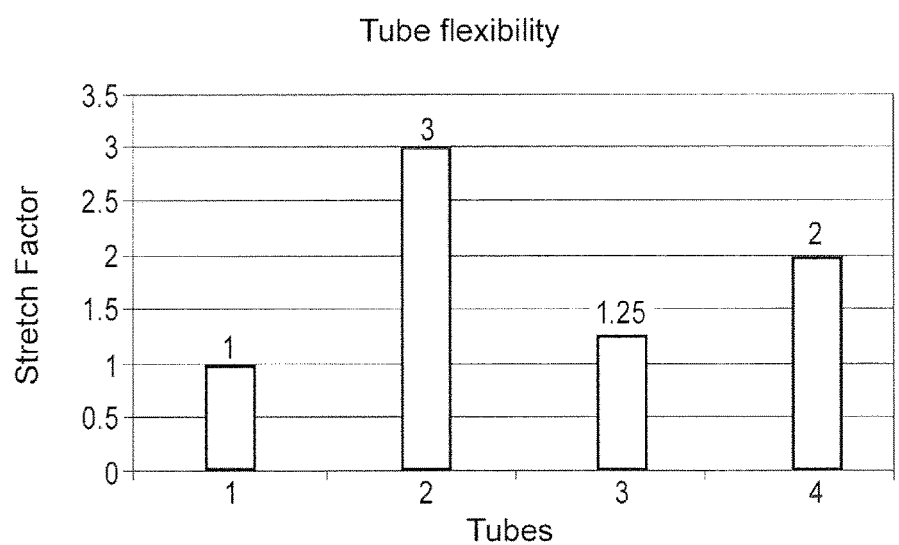
FIG. 16 is a chart of tube stretch factors or ratios of the four sample tubes listed in Table 2.

The sample embodiment of the retractable tube of sample number 4 has a moderate stretch ratio compared to prior art masks as is evident from Table 2 below. FIG. 16 charts the stretch ratios/factors for comparison purposes.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A retractable tube for use in a respiratory apparatus for delivering a pressurized flow of breathable gas to a patient, wherein the tube has an internal diameter of about 30 mm or less, a weight per unit length of about 500 g/m or less, and an unextended length of about 2 m or less, wherein the retractable tube comprises an inextensible portion and a portion that is extensible in a range of about 40%-400% of its unextended length in response to force applied to the tube, the extensible portion being configured to return the tube to its unextended length in the absence of force, or reduced force, applied to the tube.

2. A retractable tube according to claim 1, wherein the tube comprises a helical spring provided at the extensible portion.

3. A retractable tube according to claim 2, wherein the spring is provided on an inner surface of the tube at the extensible portion.

4. A retractable tube according to claim 2, wherein the spring is provided on an outer surface of the tube at the extensible portion.

5. A retractable tube according to claim 2, wherein the extensible portion comprises an inner surface and an outer surface and the spring is provided between the inner surface and the outer surface.

6. A retractable tube according to claim 2, wherein the spring is formed of plastic.

7. A retractable tube according to claim 2, wherein the spring is formed of metal.

8. A retractable tube according to claim 2, wherein the extensible portion is bowed outwardly between coils of the spring.

9. A retractable tube according to claim 2, wherein the extensible portion is bowed inwardly between coils of the spring.

10. A retractable tube according to claim 2, wherein the spring has a spring constant of about 25 N/m or less.

11. A retractable tube according to claim 2, wherein the spring has a spring constant of about 7 N/m.

12. A retractable tube according to claim 1, wherein the extensible portion comprises a plurality of bellows.

13. A retractable tube according to claim 1, wherein the retractable tube comprises a biocompatible material.

14. A retractable tube according to claim 1, wherein the retractable tube is comprised entirely of biocompatible materials.

15. A retractable tube according to claim 1, wherein the inextensible portion and the extensible portion are integrally formed.

16. A retractable tube according to claim 1, wherein the inextensible portion and the extensible portion are formed separately and connected by a connector.

17. A retractable tube according to claim 16, wherein the connector comprises a C-shaped clip.

18. A retractable tube according to claim 1, wherein the extensible portion comprises a looped portion.

19. A retractable tube according to claim 18, further comprising a retractable cord connected to the looped portion, the retractable cord being configured to extend and retract as the loop portion is extended and retracted.

20. A retractable tube according to claim 18, further comprising a winding mechanism configured to bias the retractable cord into a retracted position.

21. A retractable tube according to claim 1, wherein the extensible portion comprises a plurality of connecting rings and an elastic member that connects the connecting rings.

22. A retractable tube according to claim 1, wherein the extensible portion comprises an internal diameter of about 12 mm.

23. A retractable tube according to claim 1, wherein the extensible portion comprises an internal diameter of about 13.3 mm.

24. A retractable tube according to claim 1, wherein the extensible portion comprises an internal diameter of about 8 mm.

25. A retractable tube according to claim 1, wherein the extensible portion is extensible in a ratio of about 2:3.

26. A retractable tube according to claim 1, wherein the retractable tube is extensible by at least 40% of its unextended length.

27. A retractable tube according to claim 1, wherein the retractable tube is extensible by at least 60% of is unextended length.

28. A retractable tube according to claim 1, wherein the retractable tube is extensible by at least 100% of its unextended length.

29. A retractable tube according to claim 1, wherein the retractable tube is extensible to about 400% of is unextended length.

30. A method of delivering a flow of pressurized breathable gas from a flow generator configured to generate the pressurized flow of breathable gas to a patient interface configured to engage a patient's face and deliver the pressurized flow of breathable gas to the patient's airways, the method comprising:
    connecting the flow generator and the patient interface using a retractable hose with an extensible portion;
    anchoring the extensible portion at a fixed location only at one end of the extensible portion or only at both ends of the extensible portion; and
    dynamically adjusting the extensible portion in response to movement of the patient's head to maintain a compact arrangement of the hose close to the patient's body,
    wherein maintaining the compact arrangement comprises guiding movement of the hose across the patient's torso and/or adjusting a length of the extensible portion when the ends of the hose are as far apart as, or farther apart than, an unextended length of the extensible portion.

31. The method of claim 30 further comprising applying a biasing force to the hose to dynamically adjust the hose in response to movement of the patient's head.

32. A mask system for a patient, comprising:
a patient interface;
a tube provided to the patient interface; and
a tube arrangement adjustment device built into or formed separately from the tube and adapted to dynamically guide movement of the tube across the patient's body to maintain a compact arrangement of the tube close to the patient regardless of positioning of the patient's head.

33. A mask system according to claim 32, wherein the tube arrangement adjustment device comprises a retracting mechanism provided to the tube.

34. A mask system according to claim 33, wherein the retracting mechanism is integrally formed with the tube.

35. A mask system according to claim 33, wherein the retracting mechanism is separately connected to the tube.

36. A mask system according to claim 33, wherein the retracting mechanism comprises a retractable cord configured to extend and retract.

37. A mask system according to claim 36, wherein when retracted, the cord positions a portion of the tube to form a loop shape.

38. A mask system according to claim 17, wherein the tube arrangement adjustment device further comprises a winding mechanism configured to bias the retractable cord into a retracted position.

39. A mask system according to claim 38, wherein the winding mechanism is attached to the patient's body.

40. A mask system according to claim 32, wherein the tube is length-adjustable.

41. A retractable tube for use in a respiratory apparatus for delivering a pressurized flow of breathable gas to a patient, the retractable tube comprising:
at least one helical spring formed of a coiled strand with a plurality of coils, the strand having a diameter that varies and is between 0.1 mm-5 mm; and
a cover that covers an inside of the coils, or an outside of the coils, or both the inside and outside of the coils, wherein the cover is formed of biocompatible material, the retractable tube has an internal diameter of about 30 mm or less, a weight per unit length of about 500 g/m or less, and an unextended length of about 2 m or less, at least a portion of the retractable tube is extensible in a range of about 40%-400% of it unextended length in response to force applied to the tube, and the at least one helical spring is configured to return the retractable tube to its unextended length in the absence of force, or reduced force, applied to the retractable tube and has a spring constant of about 25 N/m or less.

42. A retractable tube according to claim 41, wherein the strand has a polygonal cross section.

43. A retractable tube according to claim 41, wherein a pitch of the coils is between about 2 m-9 mm.

44. A retractable tube according to claim 43, wherein the pitch of the coils is between about 3 mm-6 mm.

45. A retractable tube according to claim 44, wherein the pitch of the coils is about 4.8 mm.

46. A retractable tube according to claim 41, wherein a pitch of the coils varies.

47. A retractable tube according to claim 41, wherein the at least one helical spring is formed of biocompatible material.

48. A retractable tube according to claim 47, wherein the at least one helical spring is formed of a polyester elastomer.

49. A retractable tube according to claim 41, wherein the at least one helical spring is formed of metal.

50. A retractable tube according to claim 41, wherein the at least one helical spring is formed of magnetic material.

51. A retractable tube according to claim 41, wherein the at least one helical spring is formed of a material having a tensile modulus of between about 150-250 MPa.

52. A retractable tube according to claim 51, wherein the tensile modulus of the material is between about 160-240 MPa.

53. A retractable tube according to claim 52, wherein the tensile modulus of the material is between about 160-220 MPa.

54. A retractable tube according to claim 53, wherein the tensile modulus of the material is between about 180-200 MPa.

55. A retractable tube according to claim 54, wherein the tensile modulus of the material is about 180 MPa.

56. A retractable tube according to claim 54, wherein the tensile modulus of the material is about 188 MPa.

57. A retractable tube according to claim 41, wherein the cover is molded onto the at least one helical spring.

58. A retractable tube according to claim 57, wherein the cover is applied to the at least one helical spring when the at least one helical spring is in an extended state.

59. A retractable tube according to claim 41, wherein the cover is wound onto the at least one helical spring.

60. A retractable tube according to claim 59, wherein the cover is applied to the at least one helical spring when the at least one helical spring is in an extended state.

61. A retractable tube according to claim 41, wherein the at least one helical spring applies a retracting force to the retractable tube when the at least one helical spring is in an unextended state.

62. A retractable tube according to claim 41, wherein the diameter of the coils of the at least one helical spring varies.

63. A retractable tube according to claim 41, wherein the at least one helical spring comprises a plurality of springs.

64. A retractable tube according to claim 63, wherein at least one of the plurality of helical springs has a coil diameter that differs from at least one other of the plurality of helical springs.

65. A retractable tube according to claim 41, wherein the biocompatible material of the cover comprises plastic, silicone, thermoplastic urethane, or combinations thereof.

66. A retractable tube according to claim 41, wherein the retractable tube is extensible by at least 40% of its unextended length.

67. A retractable tube according to claim 41, wherein the retractable tube is extensible by at least 60% of is unextended length.

68. A retractable tube according to claim 41, wherein the retractable tube is extensible by at least 100% of its unextended length.

69. A retractable tube according to claim 41, wherein the retractable tube is extensible to about 400% of is unextended length.

70. A retractable tube according to claim 41, wherein the at least one helical spring is comprises a coiled strand having a diameter of between about 1 mm-4 mm.

71. A retractable tube according to claim 41, wherein the at least one helical spring comprises a coiled strand having a diameter of between about 1.5 mm-2.5 mm.

* * * * *

UNITED STATES PATENT AND TRADEMARK OFFICE
CERTIFICATE OF CORRECTION

| | | |
|---|---|---|
| PATENT NO. | : 10,034,995 B2 | Page 1 of 1 |
| APPLICATION NO. | : 12/211896 | |
| DATED | : July 31, 2018 | |
| INVENTOR(S) | : Kooij et al. | |

It is certified that error appears in the above-identified patent and that said Letters Patent is hereby corrected as shown below:

In the Claims

Claim 27, Column 12, Line 37, "retractable tube is extensible by at least 60% of is extended length," should be corrected to -- retractable tube is extensible by at least 60% of its extended length --.

Claim 29, Column 12, Line 42, "retractable tube is extensible by at least 400% of is extended length," should be corrected to -- retractable tube is extensible by at least 400% of its extended length --.

Claim 38, Column 13, Line 23, "A mask system according to claim 17," should be corrected to -- A mask system according to claim 37 --.

Claim 67, Column 14, Line 50, "retractable tube is extensible by at least 60% of is extended length," should be corrected to -- retractable tube is extensible by at least 60% of its extended length --.

Claim 69, Column 14, Line 55, ""retractable tube is extensible by at least 400% of is extended length," should be corrected to -- retractable tube is extensible by at least 400% of its extended length --.

Signed and Sealed this
Thirtieth Day of October, 2018

Andrei Iancu
*Director of the United States Patent and Trademark Office*